United States Patent
Hubert-Pfalzgraf et al.

(10) Patent No.: US 7,982,063 B2
(45) Date of Patent: Jul. 19, 2011

(54) MINERAL/ORGANIC COMPOSITE MATERIAL

(75) Inventors: Liliane Georgette Hubert-Pfalzgraf, Saint Andre (FR); Eugène Hubert, legal representative, St-Andre (FR); Stephane Daniele, Villeurbanne (FR)

(73) Assignees: Centre National de la Recherche Scientifique (C.N.R.S.), Paris (FR); UCBL Universite Claude Bernard de Lyon 1, Villeurbanne Cedex (FR)

( * ) Notice: Subject to any disclaimer, the term of this patent is extended or adjusted under 35 U.S.C. 154(b) by 563 days.

(21) Appl. No.: 11/990,007

(22) PCT Filed: Aug. 4, 2006

(86) PCT No.: PCT/FR2006/001903
§ 371 (c)(1),
(2), (4) Date: Jul. 29, 2008

(87) PCT Pub. No.: WO2007/017586
PCT Pub. Date: Feb. 15, 2007

(65) Prior Publication Data
US 2010/0121088 A1    May 13, 2010

(30) Foreign Application Priority Data
Aug. 5, 2005  (FR) .................................. 05 08383

(51) Int. Cl.
C07F 7/00  (2006.01)
C07F 1/00  (2006.01)

(52) U.S. Cl. ............ 556/51; 556/55; 556/105; 556/114; 534/16

(58) Field of Classification Search ............... 556/51, 556/55, 105, 114; 534/16
See application file for complete search history.

(56) References Cited

U.S. PATENT DOCUMENTS
5,593,781 A    1/1997  Nass et al.

FOREIGN PATENT DOCUMENTS
WO    WO 93/21127        10/1993
WO    WO 2005/094156 A2  10/2005

OTHER PUBLICATIONS

Schnitzler et al. "Preparation and Characterization of Novel Hybrid materials Formed from $(Ti,Sn)O_2$ Nanoparticles and Polyaniline." Nov. 1, 2003. *Chem. Mater.*, vol. 15, No. 24, pp. 4658-4665.
Goutailler et al. "Low temperature and aqueous sol-gel deposit of photocatalytic active nanoparticulate $TiO_2$." Dec. 12, 2002 *J. Mater. Chem.*, 2003, vol. 13, pp. 342-346.

*Primary Examiner* — Porfirio Nazario Gonzalez
(74) *Attorney, Agent, or Firm* — Oliff & Berridge, PLC

(57) ABSTRACT

The invention relates to a composite material comprising nanoparticles of at least one metal derivative and at least one type of carboxylic and/or sulfonic acid derivative organic compound chemically bound in a covalent manner with said nanoparticles by means of at least one carboxylic and/or sulfonic function.

23 Claims, 2 Drawing Sheets

MINERAL/ORGANIC COMPOSITE MATERIAL

The invention relates to a composite material comprising nanoparticles of at least one metal derivative, said nanoparticles being grafted by carboxylic or sulphonic organic acid derivatives.

"Mineral/organic" composite materials are of ever-increasing benefit in numerous fields.

Various research projects published in scientific articles demonstrate the importance of these composite materials, and some even propose specific methods for preparing a particular composite material. Examples of works in this field include those by D. C. Schnitzler et al. (*Chem. Mater.*, 15, (2003), 4658-4665) relating to hybrid nanoparticles (Ti, Sn)$O_2$ with adsorbed aniline, which is then polymerised in its conducting emeraldine form.

The method of preparation by the sol-gel route described by S. Daniele et al. (*J. Mater. Chem.*, 13, (2003), 342-346) is a method which is particularly suitable for the synthesis of titanium dioxide nanoparticles.

The inventors have now found that it is possible to prepare nanoparticles of metal derivatives, for example of titanium oxide, onto which are covalently grafted carboxylic acid and/or sulphonic acid type organic compounds, in particular carboxylic and/or sulphonic acids which are known for their intrinsic properties as protectants against ultraviolet radiation, hereinafter called "organic sun filters".

Therefore, the present invention first relates to a composite material comprising:
nanoparticles of at least one metal derivative and
at least one organic compound derived from a carboxylic and/or sulphonic acid which is covalently chemically bound to said nanoparticles via at least one carboxylic and/or sulphonic functional group.

In the composite material according to the invention, the metal derivative must be able to take a form which allows one or more covalent bonds to be created with the carboxylic and/or sulphonic acid derivative.

In general, said acid derivative is covalently chemically bound to said metal derivative.

Therefore, the metal derivative is advantageously a metal in oxidised or reduced form, preferably in oxidised form. By "oxidised or reduced form" is principally meant that the metal is basically not in the form of a zero valent atom. According to an especially advantageous embodiment of the present invention, the metal derivative is a metal oxide.

Depending on the applications envisaged for the composite material according to the invention, it is preferable that said metal derivative is not toxic for man or the environment. It is also preferable that the metal derivative has semiconductor properties and, in particular, that it is capable of absorbing ultraviolet radiation.

Therefore, the metal of said metal derivative which can be used in the composite materials according to the present invention is preferably selected from the group consisting of titanium, zinc, tin, cerium, zirconium, copper, and mixtures thereof, and preferably from the group consisting of titanium, zinc, tin, cerium, and mixtures thereof.

According to a preferred embodiment, the metal derivative is a metal oxide and is selected, in particular, from titanium dioxide ($TiO_2$), zinc monoxide (ZnO), tin dioxide ($SnO_2$), the cerium oxides ($Ce_2O_3$ and $CeO_2$), zirconium oxide ($ZrO_2$), the copper oxides (CuO and $Cu_2O$), and mixtures thereof. Quite preferably, the metal derivative contains titanium in its oxidised form, titanium dioxide ($TiO_2$).

Metal derivatives having semiconductor properties are further preferred. Thus, for example, of the aforementioned oxides, titanium dioxide ($TiO_2$), zinc monoxide (ZnO), tin dioxide ($SnO_2$) and cerium dioxide ($CeO_2$), and mixtures thereof have these semiconductor properties and represent preferred metal derivatives.

The organic compound grafted on the nanoparticles is an acid, salt or ester corresponding to the formula:

$$R''\text{-}A\text{-}Y$$

in which
R" represents a hydrocarbon radical optionally containing one or more heteroatoms selected from oxygen, nitrogen, sulphur, phosphorus, boron and selenium;
A-Y represents a carboxylic group COOY or sulphonic group SO3Y, where Y is selected from:
  a hydrogen atom;
  a cation derived from a primary, secondary, tertiary or quaternary amine, or else an ammonium cation;
  a cation of an alkali metal or of an alkaline-earth metal from the periodic table;
  a cation of a transition element from groups 3, 4, 5, 6, 7, 8, 9, 10, 11 and 12 of the periodic table or a cation of an element from groups 13, 14, 15 and 16 of the periodic table or a cation of an element from the lanthanide series of the periodic table, namely Ce, Pr, Nd, Pm, Sm, Eu, Gd, Tb, Dy, Ho, Er, Tm, Yb and Lu; and
  a saturated or unsaturated, linear, branched or cyclic hydrocarbon group containing 1 to 30 carbon atoms.

The expression "acid derivative" in the present invention denotes the organic compound as defined hereinbefore (acid, salt or ester) comprising at least one carboxylic acid functional group COOY and/or at least one sulphonic acid functional group $SO_3Y$, of which at least one Y atom is missing.

It is further preferred that the organic compound comprising at least one carboxylic and/or sulphonic functional group further comprises at least one aromatic ring. Even more preferably, at least one carboxylic acid functional group and/or sulphonic acid functional group is carried on at least one aromatic ring.

Therefore, the organic compounds which may be used for the composite materials of the present invention are advantageously selected from any organic compound comprising at least one carboxylic acid functional group and/or at least one sulphonic acid functional group, optionally in the form of a salt or ester, examples including carboxylic acids, sulphonic acids, but also the aforementioned acids also comprising other functional groups, such as natural or non-natural amino acids, aminosulphonic acids, carboxylic and/or sulphonic keto acids, carboxylic and/or sulphonic hydroxy acids and others, whether linear, branched, cyclic, saturated, unsaturated and/or aromatic.

It is further preferred that the organic compound comprising at least one carboxylic acid functional group and/or at least one sulphonic acid functional group contains at least 4 carbon atoms, more preferably at least 5 carbon atoms, even more preferably at least 6 carbon atoms, advantageously at least 7 carbon atoms, and most preferably at least 8 carbon atoms.

According to an embodiment of the invention, the metal derivative nanoparticles are grafted by an organic compound which is known for its intrinsic ultraviolet radiation blocking/absorbing properties and generally known by the name "organic sun filter". In particular, the sun filters concerned are any organic compounds comprising at least one carboxylic acid functional group and/or at least one sulphonic acid functional group which absorb UV radiation in the general wavelength range from 250 nm to 400 nm, without this being a limit.

Examples of organic sun filters which are suitable for the present invention include, in a non-limiting manner, the compounds sold under the trade names PABA (para-aminobenzoic acid), Uvinul MS-40 ® (5-benzoyl-4-hydroxy-2-methoxybenzene-sulphonic acid), Eusolex 232® (2-phenylbenzimidazole-5-sulphonic acid), Mexoryl SL® (3,3'-(1,4-phenylidene-dimethylidene)bis-(7,7-dimethyl-2-oxobicyclo[2,2,1]hept-1-yl-methane-sulphonic) acid and the salts thereof), Mexoryl SX® (α-(oxo-2-bornylidene-3)-toluene-4-sulphonic acid and the salts thereof), Parsol 340® (2-ethylhexyl 2-cyano-3,3-diphenylacrylate), octyl 4-methoxycinnamate, Uvinul P-25® (ethoxylated ethyl 4-aminobenzoate, and other similar filters.

The following sun filters are particularly preferred:
PABA or para-aminobenzoic acid;
Eusolex 232® or 2-phenylbenzimidazole-5-sulphonic acid; and
Uvinul MS-40® or 5-benzoyl-4-hydroxy-2-methoxybenzenesulphonic acid.

According to a quite particularly preferred aspect of the present invention, the composite material according to the present invention comprises titanium dioxide nanoparticles covalently grafted by at least one carboxylic and/or sulphonic acid derivative, via at least one carboxylic and/or sulphonic functional group.

In particular, the composite material according to the present invention comprises titanium dioxide nanoparticles which are covalently grafted by at least one carboxylic and/or sulphonic acid derivative, by means of at least one carboxylic and/or sulphonic functional group, said acid being selected from the group consisting of para-aminobenzoic acid, 5-benzoyl-4-hydroxy-2-methoxybenzenesulphonic acid, 2-phenylbenzimidazole-5-sulphonic acid, as well as the salts or esters thereof.

It is nevertheless to be understood that in the composite material of the present invention, all the metal atoms can be bound to at least one carboxylic and/or sulphonic acid derivative, although only some of the metal atoms of the nanoparticle can be chemically bound to at least one carboxylic and/or sulphonic acid derivative, the other metal atoms, which are not chemically bound to an organic compound, then being present in the nanoparticle in oxidised and/or reduced form, preferably in oxidised form, more preferably in the form of an oxide. By oxidised and/or reduced form it is principally meant that the metal is basically not in the form of a zero valent atom.

Schematically, and theoretically, the composite material is in the form of nanoparticles of metal derivative, onto the surface of which at least one carboxylic and/or sulphonic acid derivative is grafted; in particular, the nanoparticles have a surface which is substantially covered with said derivatives, which are chemically bound to said nanoparticles of metal derivative.

Therefore, the composite material according to the invention is in the form of metal derivative particles which are all functionalised by at least one carboxylic and/or sulphonic acid derivative and optionally in the crystalline state, said particles having a mean particle size from approximately one nanometer to several tens of nanometers, preferably a particle size of between 1 nm and 50 nm, more preferably between 1 nm and 30 nm, even more preferably between 1 nm and 20 nm, advantageously between 2 nm and 10 nm.

It should also be understood that said carboxylic and/or sulphonic acid derivative are grafted onto the surface of the nanoparticles, and can nevertheless also be included in the nanoparticle itself.

The nanoparticles of the composite material according to the present invention may in particular be obtained by means of the method of preparation described below in the present description, and for example by a similar process to that disclosed by S. Daniele et al. (*J. Mater. Chem.*, 13, (2003), 342-346).

Therefore, and according to a further subject-matter of the present invention, the composite material according to the present invention can advantageously be obtained by inorganic polymerisation (sol-gel method), in a single step, from at least one hydrolysable precursor of a at least one metal which has been modified with at least one carboxylic and/or sulphonic acid as defined hereinbefore.

By hydrolysable precursor of a metal it is meant, for example, the alkoxides, amides or halides of one or more of the metals disclosed above, more specifically of the metals of which the oxidised forms have semiconductor properties. Preferably, the precursors are selected from metal alkoxides, more preferably from the alkoxides of the following formula (I):

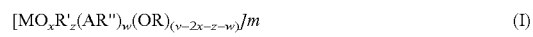
$$[MO_xR'_z(AR'')_w(OR)_{(v-2x-z-w)}]m \quad (I)$$

in which:
M represents an atom of a metal advantageously selected from titanium, zinc, cerium, zirconium, and copper;
O represents an oxygen atom
v is the valency of the metal M;
x is a number greater than or equal to zero and less than v/2; (0≦x<v/2);
z is a number greater than or equal to zero and less than v; (0≦z<v);
w is a number greater than zero and less than or equal to v; (0<w≦v);
m is the rate of oligomerisation of the precursor of formula (I) and represents an integer greater than or equal to 1, preferably from 1 to 100 inclusive;
2x+z+w≦v;
A represents a $CO_2$ or $SO_3$ group;
R is selected from a linear or branched alkyl radical containing 1 to 30 carbon atoms, a substituted or unsubstituted cycloalkyl radical containing 3 to 9 endocyclic carbon atoms, and a substituted or unsubstituted aryl radical containing 6 to 10 atoms;
R' represents a halogen atom selected from fluorine, chlorine, bromine, iodine and astatine, or represents the hydroxyl group; and
R" represents a hydrocarbon radical optionally containing one or more heteroatoms selected from oxygen, nitrogen, sulphur, phosphorus, boron and selenium.

According to a particularly preferred embodiment of the invention, the metal is titanium. The compound of formula (I) becomes the compound of the following formula ($I_{Ti}$):

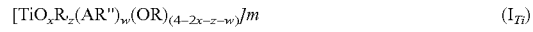
$$[TiO_xR_z(AR'')_w(OR)_{(4-2x-z-w)}]m \quad (I_{Ti})$$

in which:
x is a number greater than or equal to zero and less than 2; (0≦x<2);
z is a number greater than or equal to zero and less than 4; (0≦z<4);
w is a number greater than zero and less than or equal to 4; (0<w≦4);
2x+z+w≦4; and
O, m, R, R' and R" are as defined above;

According to an advantageous variant, the inorganic polymerisation of at least one hydrolysable precursor of formula (I) and/or (I$_{Ti}$) can be carried out in the presence of another hydrolysable compound, for example an alkoxide, amide or halide, as defined above, optionally unmodified by an organic compound, and in particular, of another hydrolysable metal compound which does not comprise any carboxylic and/or sulphonic acid residue.

The simultaneous inorganic polymerisation (or hydrolysis) of precursors modified by at least one carboxylic and/or sulphonic acid and of "pure" (i.e. unmodified) precursors, according to the method of the invention, allows an alteration of the density of organic compounds on the surface of the metal nanoparticle.

By way of non-limiting example, the inorganic polymerisation of at least one hydrolysable precursor of formula (I) can be carried out in the presence of another hydrolysable compound of the following formula (II):

$$[M'(OR)_{v'}]_{m'} \qquad (II)$$

in which:
M' represents an atom of a metal which is the same as or different from M, selected from titanium, zinc, cerium, zirconium, and copper;
m' is the rate of oligomerisation of the compound (II) and represents an integer greater than or equal to 1, preferably from 1 to 100 inclusive;
v' is the valency of the metal M'; and
R is selected from a linear or branched alkyl radical containing 1 to 30 carbon atoms, a substituted or unsubstituted cycloalkyl radical containing 3 to 9 endocyclic carbon atoms, and a substituted or unsubstituted aryl radical containing 6 to 10 atoms;

When the metal is titanium, the compound of formula (II) becomes the compound of the following formula (II$_{Ti}$):

$$[Ti(OR)_4]_{m'} \qquad (II_{Ti})$$

in which R and m' are as defined above.

The inorganic polymerisation referred to above may be carried out in a hydro-organic medium which is either mostly or purely water. The benefit of working in a purely aqueous medium is solely due to the concern of respecting the current rules and guidelines on the protection of the environment and on toxicity, particularly when the composite material of the invention is likely to come into contact with living organisms, plants, animals or humans.

When an organic solvent is present (inorganic polymerisation in a hydro-organic medium), said solvent is advantageously selected from the alcohols, preferably the monoalcohols, and for example from methanol, ethanol, n-propanol, iso-propanol, n-butanol, iso-butanol and tert-butanol, and mixtures thereof in any proportions.

This list is not in any way limiting and other solvents may be used, such as unsaturated hydrocarbons, for example toluene, saturated hydrocarbons, for example hexane, aliphatic ethers or cyclic ethers, for example diethyl ether or tetrahydrofuran, as well as solvents of the dimethyl formamide or dimethyl sulphoxide type. Mixtures of two or more of the solvents mentioned here can also be used.

According to a preferred embodiment of the method, the inorganic polymerisation takes place in the presence of at least one ionic salt. The appropriate ionic salts can be selected from nitrates, halides, sulphates, or alkali, alkaline-earth or ammonium phosphates, and mixtures of two or more of these in any proportions. By way of non-limiting example, the ionic salt can be selected from potassium nitrate, lithium bromide, magnesium sulphate, and tetra-n-butyl ammonium bromide. A preferred ionic salt is tetra-n-butyl ammonium bromide.

The quantity of ionic salt which is used can vary greatly, and is generally between 0.5% and 20% by weight, preferably between 1% and 10% by weight, based on the original metal precursor.

The inorganic polymerisation reaction takes place when at least one hydrolysable metal precursor modified by at least one carboxylic and/or sulphonic acid as defined hereinbefore, optionally in the presence of another unmodified hydrolysable precursor, comes into contact with water or a water/solvent mixture.

The amount of water which is necessary for the inorganic polymerisation reaction can also vary greatly, and in general 100 ml of water is used for a quantity of metal precursor(s) between 0.1 g and 10 g. The amount of organic solvent or of organic solvent mixture is generally between 0% and 20% by weight based on the amount of water used.

The inorganic polymerisation reaction is generally carried out at a pH of between 4 and 8, more generally between 5 and 7.

This inorganic polymerisation can be carried out at ambient temperature or at a temperature between the ambient temperature and the reflux temperature of the reaction medium, for example at a temperature between 15° C. and 150° C., advantageously between 25° C. and 130° C., preferably between 80° C. and 120° C., preferably at approximately 100° C.

However, the heating of the reaction medium is not necessary, but does promote the formation of nanometric particles in crystalline form, rather than amorphous form, i.e. the composite material obtained displays diffraction bands under X-ray radiation.

The inorganic polymerisation reaction is generally carried out at normal atmospheric pressure, for a duration varying from a few tens of minutes to a few hours, generally between one and three hours, for example two hours.

The solid is extracted from the reaction medium, by conventional methods known to the person skilled in the art, for example by centrifuging, washed, rinsed, then dried.

This polymerisation reaction allows a solid to be obtained in a single step and in very moderate conditions, which solid is ready for use and is generally crystalline, in the form of nanometric particles, and is functionalised, i.e. has at least one carboxylic and/or sulphonic acid derivative chemically bound thereto by covalent bonding (or coordination).

This composite material is thus obtained in a very economical manner in a single step and in an aqueous or hydro-organic medium, starting from modified metal precursors which can easily be obtained, and in particular starting from alkoxides which have been modified with one or more carboxylic and/or sulphonic acids, salts or esters of formula R"-A-Y, as defined above. It should be understood that when the organic sun filter is an ester, (Y being a saturated or unsaturated, linear, branched or cyclic hydrocarbon group, containing 1 to 30 carbon atoms), said ester must be hydrolysed beforehand in acid or in salt, by conventional hydrolysis methods known to the person skilled in the art.

The aforementioned metal precursors are known, commercially available, or easily synthesised using known procedures which emerge from standard chemistry works, from publications, from patents, from "Chemical Abstracts", or from the Internet.

Furthermore, the composite material according to the invention has a high functionalisation level and efficient adhesion, via covalent bonding, of the carboxylic and/or sulphonic acid derivative, and therefore has a higher stability in any medium of which the pH is between 2 and 10.

By "functionalisation level" is meant the weight ratio of organic component to mineral component in the composite material. This functionalisation level is generally between 0.1% and 30%, preferably between 0.5% and 20%, advantageously between 1% and 15%, for example between 1.5% and 10%.

The composite material according to the invention takes the form of nanometric particles such as have just been defined, which have the advantage of being dispersible in a manner compatible with the majority of envisaged applications. In fact, good dispersion of the nanoparticles demonstrates low aggregation between the nanoparticles, as well as a relatively low agglomerate particle size.

In general, the composite materials of the present invention have an agglomerate particle size between 100 nm and 3000 nm, most often between 150 nm and 2500 nm, in particular between 160 nm and 2200 nm, for functionalisation levels of about 1.5% to 8%.

The inventors have demonstrated that the dispersion varies depending on the functionalisation level defined above, and on the nature of the sun filter grafted onto the nanoparticles.

The composite material of the present invention is suitable for numerous fields of use, such as, but not exclusively, organic and/or inorganic chemical synthesis, the pharmaceutical industry, medical diagnostics, medical imaging, cosmetics, the fields of coatings, inks, paints, etc.

For example, the composite material according to the present invention may be used as a protectant against ultraviolet radiation in cosmetic sun screens.

The following examples are given purely by way of illustration and are not of a limiting character.

EXAMPLE 1

Preparation of a Composite
$TiO_2$/Para-Aminobenzoic Acid Material

Starting from Titanium Para-Aminobenzoate
Tri-Isopropoxide in an Aqueous Medium

| | |
|---|---|
| $[Ti(OC_3H_7)_3(O_2CC_6H_4NH_2)]_m$ | 0.90 g |
| Tetra-n-butylammonium bromide (N"$Bu_4Br$) | 0.08 g |
| Water ($H_2O$) | 50.00 g |

The $[Ti(OC_3H_7)_3(O_2CC_6H_4NH_2)]_m$ is obtained by an equimolar reaction between the titanium tetra-isopropoxide $[Ti(OC_3H_7)4]$ and the para-aminobenzoic acid ($HO_2CC_6H_4NH_2$, PABA). The index m represents the number of precursors involved in a crystal lattice.

The $[Ti(OC_3H_7)_3(O_2CC_6H_4NH_2)]_m$ is added into the aqueous solution of N"$Bu_4Br$ which has been brought to reflux, and is stirred for 2 hours while maintaining the reflux. The solid is recovered by centrifuging then washed in water and in ethanol. After drying at 70° C. for 20 hours, the material is ready for use. The material has a functionalisation level of 7.6% by weight.

EXAMPLE 2

Preparation of a Composite $TiO_2$/PABA Material

Starting from Titanium Para-Aminobenzoate
Tri-Isopropoxide, in a Hydro-Organic Medium
which is Mostly Water, in the Presence of Titanium
Alkoxide

| | |
|---|---|
| $[Ti(OC_3H_7)_3(O_2CC_6H_4NH_2)]_m$ | 0.13 g |
| Titanium tetra-isopropoxide $[Ti(OC_3H_7)_4]_m$ | 6.75 g |
| Tetra-n-butylammonium bromide (N"$Bu_4Br$) | 0.80 g |
| Isopropanol ($HOC_3H_7$) | 6.00 g |
| Water ($H_2O$) | 75.00 g |

The isopropanol solution comprising $[Ti(OC_3H_7)_3(O_2CC_6H_4NH_2)]_m+[Ti(OC_3H_7)_4]_m$ is added into the aqueous solution of N"$Bu_4Br$ which has been brought to reflux, and is stirred for 3 hours while maintaining the reflux. The solid is recovered by centrifuging then washed in water and in ethanol. After drying at 70° C. for 20 hours, the material is ready for use. The material has a functionalisation level of 1.5% by weight.

EXAMPLE 3

Preparation of a Composite $TiO_2$/Uvinul MS 40® Material

Starting from Titanium
5-benzoyl-4-hydroxy-2-methoxybenzene
sulphonate-tri-isopropoxide in an Aqueous Medium

| | |
|---|---|
| $[Ti(OC_3H_7)_3(C_{14}H_{12}O_6S)]_m$ | 0.18 g |
| Tetra-n-butylammonium bromide (N"$Bu_4Br$) | 0.01 g |
| Water ($H_2O$) | 50.00 g |

The $[Ti(OC_3H_7)_3(C_{14}H_{12}O_6S)]_m$ is obtained by an equimolar reaction between the titanium tetra-isopropoxide $[Ti(OC_3H_7)_4]$ and the 5-benzoyl-4-hydroxy-2-methoxybenzene sulphonic acid (Uvinul MS 40®).

The $[Ti(OC_3H_7)_3(C_{14}H_{12}O_6S)]_m$ is added into the aqueous solution of N"Br which has been brought to reflux, and is stirred for 2 hours while maintaining the reflux. The solid is recovered by centrifuging then washed in water and in ethanol. After drying at 70° C. for 20 hours, the material is ready for use.

EXAMPLE 4

Preparation of a Composite TiO$_2$/Uvinul MS 40® Material

Starting from Titanium 5-benzoyl-4-hydroxy-2-methoxybenzene sulphonate-tri-isopropoxide, in an Aqueous Medium which is Mostly Water, in the Presence of Titanium Alkoxide

| | |
|---|---|
| [Ti(OC$_3$H$_7$)$_3$(C$_{14}$H$_{12}$O$_6$S)]$_m$ | 0.1 g |
| Titanium tetra-isopropoxide [Ti(OC$_3$H$_7$)$_4$]$_m$ | 0.8 g |
| Tetra-n-butylammonium bromide (N"Bu$_4$Br) | 0.1 g |
| Isopropanol (HOC$_3$H$_7$) | 6.0 g |
| Water (H$_2$O) | 75.0 g |

The isopropanol solution comprising [Ti(OC$_3$H$_7$)$_3$(C$_{14}$H$_{12}$O$_6$S)]$_m$+[Ti(OC$_3$H$_7$)$_4$]$_m$ is added to the aqueous solution of N"Bu$_4$Br which has been brought to reflux, and is stirred for 3 hours while maintaining the reflux. The solid is recovered by centrifuging then washed in water and in ethanol. After drying at 70° C. for 20 hours, the material is ready for use.

All these materials have been unequivocally characterised by elemental analyses, infrared spectroscopies with Fourier transformations and visible UV, diffraction of X-rays on powder, transmission electron microscopy and photoelectronic spectroscopy.

The following description by way of reference to the attached figures will allow the object of the invention to be better understood. Where they are not mutually exclusive, the various embodiments described in the following may be combined.

Figure 1:
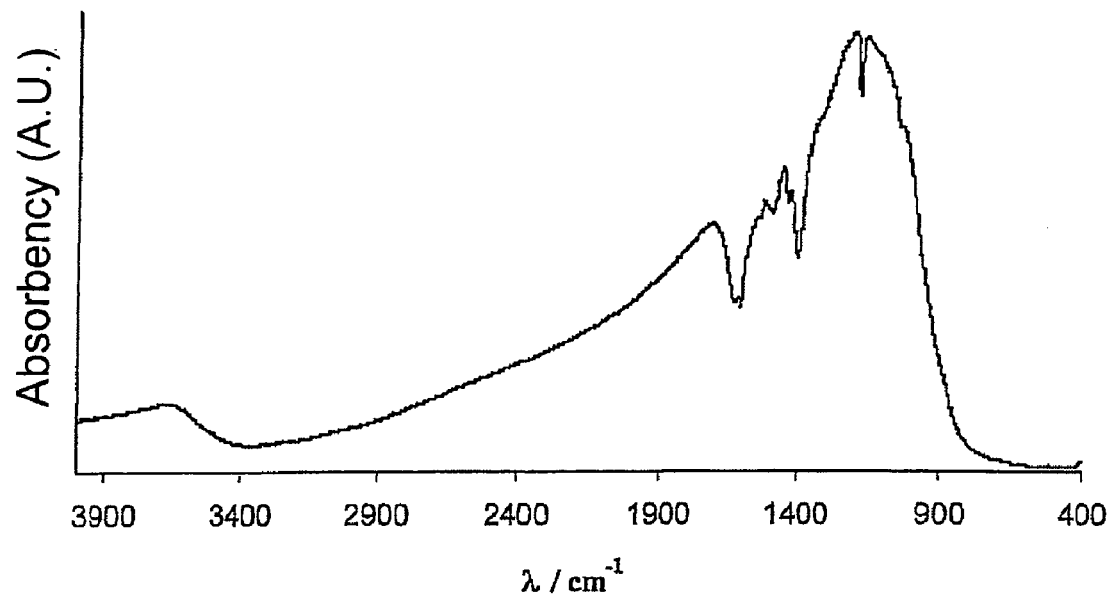
FIG. 1 is an infrared spectrum with Fourier transformation of a composite material of titanium nanoparticles grafted by Uvinul MS-40® (5-benzoyl-4-hydroxy-2-methoxybenzenesulphonic acid).
Figure 2:
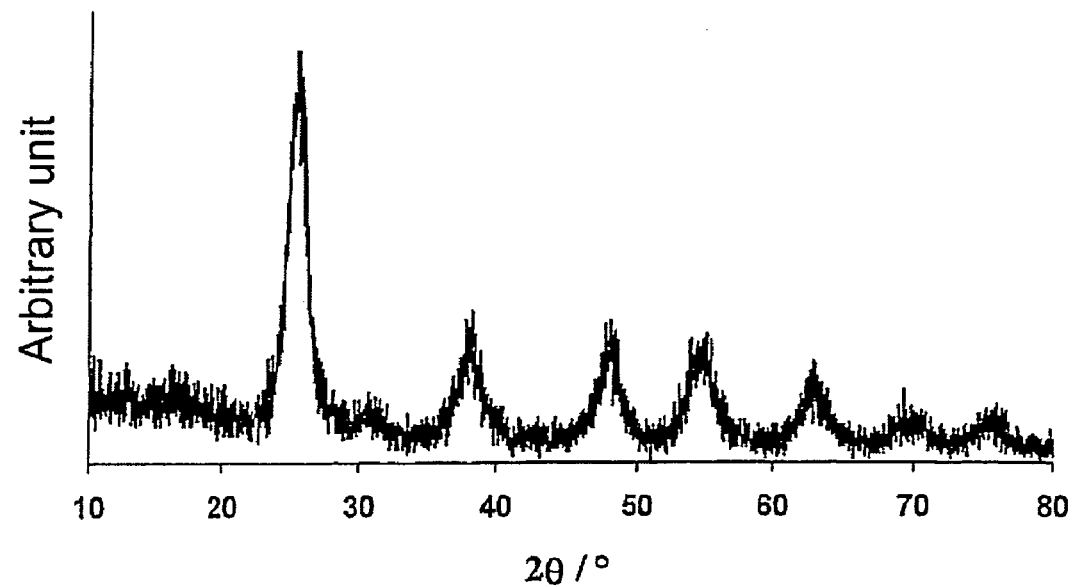
FIG. 2 is a diffraction spectrum of X rays on a composite material of titanium nanoparticles grafted by para-aminobenzoic acid (PABA).
Figure 3:
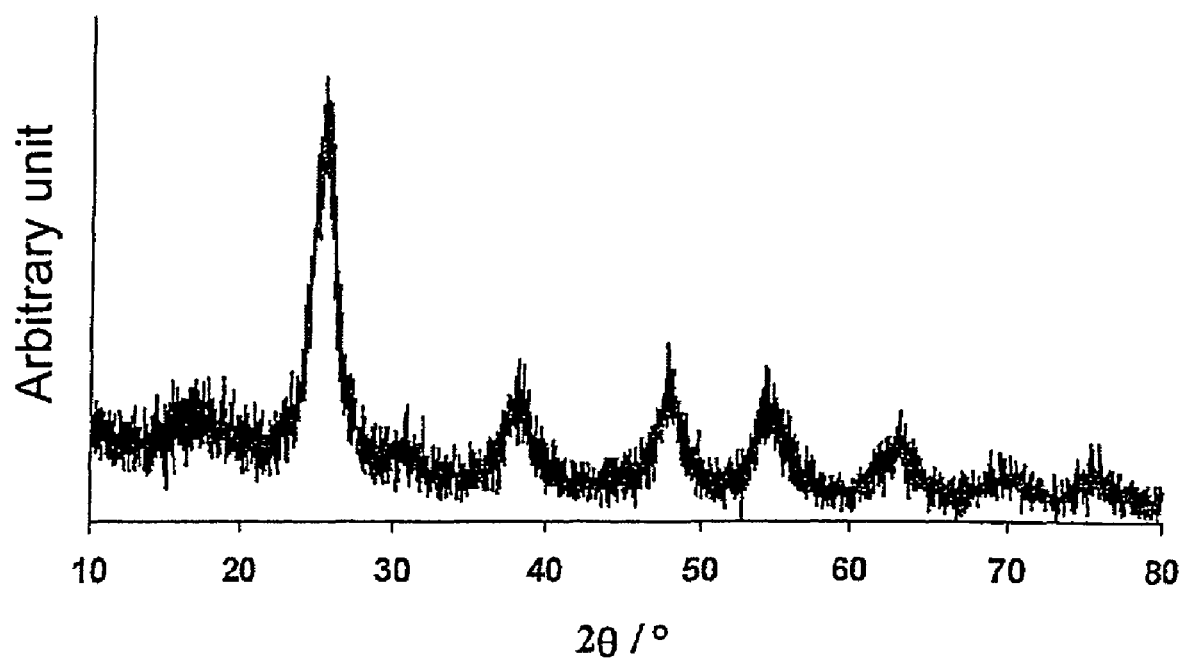
FIG. 3 is a diffraction spectrum of X rays on a composite material of titanium nanoparticles grafted by Uvinul MS-40® (5-benzoyl-4-hydroxy-2-methoxybenzenesulphonic acid).

The invention claimed is:

1. Composite material comprising:
   nanoparticles of at least one metal derivative and
   at least one organic compound derived from a carboxylic and/or sulphonic acid which is covalently chemically bound to said nanoparticles via at least one carboxylic and/or sulphonic functional group,
   wherein all the nanoparticles are functionalized.

2. Material according to claim 1, wherein said acid derivative is covalently chemically bound to said metal derivative.

3. Material according to claim 1, wherein the metal derivative is a metal in oxidised form.

4. Material according to claim 1, wherein the metal derivative is a metal oxide.

5. Material according to claim 1, wherein the metal derivative has semiconductor properties.

6. Material according to claim 1, wherein the metal of said metal derivative is selected from the group consisting of titanium, zinc, tin, cerium, zirconium, copper, and mixtures thereof.

7. Material according to claim 1, wherein the metal derivative is a metal oxide selected from titanium dioxide (TiO2), zinc monoxide (ZnO), tin dioxide (SnO2), cerium oxides (Ce2O3 and CeO2), zirconium oxide (ZrO2), copper oxides (CuO and Cu2O), and mixtures thereof.

8. Material according to claim 1, wherein the nanoparticles have a mean particle size of between 1 nm and 50 nm.

9. Material according to claim 1, wherein the functionalisation level is between 0.1% and 30%, by weight of organic component based on the mineral component.

10. Material according to claim 1, wherein the nanoparticles are in crystalline form.

11. Material according to claim 1, wherein said organic compound is selected from any linear, branched, cyclic, saturated, unsaturated and/or aromatic organic compound comprising at least one carboxylic acid functional group and/or at least one sulphonic acid functional group.

12. Material according to claim 1, wherein said organic compound is an acid, salt or ester corresponding to the formula:

R"-A-Y in which
   R" represents a hydrocarbon radical optionally containing one or more heteroatoms selected from oxygen, nitrogen, sulphur, phosphorus, boron and selenium;
   A-Y represents a carboxylic group COOY or sulphonic group SO3Y, where Y is selected from:
      a hydrogen atom;
      a cation derived from a primary, secondary, tertiary or quaternary amine, or else an ammonium cation;
      a cation of an alkali metal or of an alkaline-earth metal from the periodic table; and
      a cation of a transition element from groups 3, 4, 5, 6, 7, 8, 9, 10, 11 and 12 of the periodic table or a cation of an element from groups 13, 14, 15 and 16 of the periodic table or a cation of an element from the lanthanide series of the periodic table, namely Ce, Pr, Nd, Pm, Sm, Eu, Gd, Tb, Dy, Ho, Er, Tm, Yb and Lu; and
      a saturated or unsaturated, linear, branched or cyclic hydrocarbon group, containing 1 to 30 carbon atoms.

13. Material according to claim 1, wherein said organic compound is a sun filter selected from para-aminobenzoic acid, 5-benzoyl-4-hydroxy-2-methoxybenzene sulphonic acid, 2-phenylbenzimidazole-5-sulphonic acid, 3,3'-(1,4-phenylidenedimethylidene)bis-(7,7-dimethyl-2-oxobicyclo[2,2,1]hept-1-yl-methanesulphonic) acid and the salts thereof, α-(oxo-2-bornylidene-3)-toluene-4-sulphonic acid and the salts thereof, 2-ethyl hexyl 2-cyano-3,3-diphenylacrylate, octyl 4-methoxycinnamate), and ethoxylated ethyl 4-aminobenzoate.

14. Material according to claim 1, wherein said organic compound comprises at least one aromatic ring, and at least one carboxylic acid functional group and/or sulphonic acid functional group of said organic compound is carried on at least one aromatic ring.

15. Material according to claim 1, wherein it comprises titanium dioxide nanoparticles, at the surface of which at least one carboxylic acid and/or sulphonic acid derivative is covalently grafted via at least one carboxylic and/or sulphonic functional group.

16. Material according to claim 1, wherein it comprises titanium dioxide nanoparticles, at the surface of which at least one carboxylic acid and/or sulphonic acid derivative is covalently grafted via at least one carboxylic and/or sulphonic functional group, said acid being selected from the group consisting of para-aminobenzoic acid, 5-benzoyl-4-hydroxy-2-methoxybenzene-sulphonic acid, 2-phenylbenzimidazole-5-sulphonic acid, as well as the cosmetically acceptable salts or esters thereof.

17. Method for preparing a material comprising nanoparticles of a metal and at least one organic compound derived from carboxylic and/or sulphonic acid which is covalently bound to said nanoparticle via at least one carboxylic and/or sulphonic functional group, comprising subjecting at least one hydrolysable precursor of a metal modified by at least a carboxylic and/or sulphonic acid to inorganic polymerization in the presence of water or a mixture of water and solvent.

18. Method according to claim 17, wherein said precursor is selected from alkoxides, amides and halides of said metal.

19. Method according to claim 18, wherein said precursor corresponds to the following formula (I):

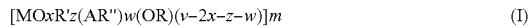

$$[MO_x R'_z (AR'')_w (OR)_{(v-2x-z-w)}]_m \quad (I)$$

in which:
- M represents an atom of a metal advantageously selected from titanium, zinc, cerium, zirconium, and copper;
- O represents an oxygen atom
- v represents the valency of the metal M;
- x is a number greater than or equal to zero and less than v/2; (0≦x<v/2);
- z is a number greater than or equal to zero and less than v; (0≦z<v);
- w is a number greater than zero and less than or equal to v; (0<w≦v);
- m is the rate of oligomerisation of the precursor of formula (I) and is an integer greater than or equal to 1;
- 2x+z+w≦v;
- A represents a CO2 or SO3 group;
- R is selected from a linear or branched alkyl radical containing 1 to 30 carbon atoms, a substituted or unsubstituted cycloalkyl radical containing 3 to 9 endocyclic carbon atoms, and a substituted or unsubstituted aryl radical containing 6 to 10 atoms;
- R' represents a halogen atom selected from fluorine, chlorine, bromine, iodine and astatine, or represents a hydroxyl group; and
- R" represents a hydrocarbon radical optionally containing one or more heteroatoms selected from oxygen, nitrogen, sulphur, phosphorus, boron and selenium.

20. Method according to claim 18, wherein said precursor corresponds to the following formula (ITi):

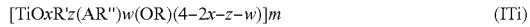

$$[TiO_x R'_z (AR'')_w (OR)_{(4-2x-z-w)}]_m \quad (ITi)$$

in which:
- x is a number greater than or equal to zero and less than 2; (0≦x<2);
- z is a number greater than or equal to zero and less than 4; (0≦z<4);
- w is a number greater than zero and less than or equal to 4; (0<w≦4);
- 2x+z+w≦4; and
- O represents an oxygen atom
- m is the rate of oligomerisation of the precursor of formula (I) and is an integer greater than or equal to 1;
- R is selected from a linear or branched alkyl radical containing 1 to 30 carbon atoms, a substituted or unsubstituted cycloalkyl radical containing 3 to 9 endocyclic carbon atoms, and a substituted or unsubstituted aryl radical containing 6 to 10 atoms;
- R' represents a halogen atom selected from fluorine, chlorine, bromine, iodine and astatine, or represents a hydroxyl group; and
- R" represents a hydrocarbon radical optionally containing one or more heteroatoms selected from oxygen, nitrogen, sulphur, phosphorus, boron and selenium.

21. Method according to claim 17, wherein the inorganic polymerisation of at least one hydrolysable precursor of formula (I) or of formula (ITi) is carried out in the presence of another hydrolysable metal compound, optionally unmodified by an organic compound.

22. Method according to claim 17, wherein the inorganic polymerisation is carried out in the presence of at least one ionic salt, which is present in a quantity of between 0.5% and 20% by weight, based on the original metal precursor.

23. Method according to claim 17, wherein the inorganic polymerisation is carried out at a temperature between ambient temperature and reflux temperature of the reaction medium.

* * * * *